United States Patent
DiBiasi

(10) Patent No.: US 7,540,858 B2
(45) Date of Patent: *Jun. 2, 2009

(54) RETRACTING SAFETY PEN NEEDLE

(75) Inventor: Michael A. DiBiasi, West Milford, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/626,236

(22) Filed: Jan. 23, 2007

(65) Prior Publication Data

US 2008/0177235 A1   Jul. 24, 2008

(51) Int. Cl.
*A61M 5/32* (2006.01)

(52) U.S. Cl. ...................................... 604/192

(58) Field of Classification Search ........... 604/181, 604/110, 188, 187, 192, 198
See application file for complete search history.

(56) References Cited

U.S. PATENT DOCUMENTS

| | | | | |
|---|---|---|---|---|
| 4,921,491 A |   | 5/1990 | Champ | 604/199 |
| 5,295,975 A | * | 3/1994 | Lockwood, Jr. | 604/198 |
| 5,300,030 A |   | 4/1994 | Crossman et al. | 604/136 |
| 5,591,138 A | * | 1/1997 | Vaillancourt | 604/263 |
| 5,620,421 A |   | 4/1997 | Schmitz | 604/135 |
| 5,637,094 A |   | 6/1997 | Stuart, Jr. et al. | 604/135 |
| 5,935,113 A | * | 8/1999 | Dysarz | 604/263 |
| 5,941,857 A |   | 8/1999 | Nguyen et al. | 604/198 |
| 5,964,739 A | * | 10/1999 | Champ | 604/263 |
| 5,984,899 A | * | 11/1999 | D'Alessio et al. | 604/198 |
| 6,039,713 A |   | 3/2000 | Botich et al. | 604/110 |
| 6,162,197 A |   | 12/2000 | Mohammad | 604/195 |
| 6,379,337 B1 |   | 4/2002 | Mohammad | 604/195 |
| 6,391,003 B1 | * | 5/2002 | Lesch, Jr. | 604/110 |
| 6,547,764 B2 | * | 4/2003 | Larsen et al. | 604/192 |
| 6,569,123 B2 |   | 5/2003 | Alchas et al. | 604/192 |
| 6,629,959 B2 | * | 10/2003 | Kuracina et al. | 604/192 |
| 6,648,858 B2 | * | 11/2003 | Asbaghi | 604/198 |
| 6,752,798 B2 | * | 6/2004 | McWethy et al. | 604/506 |
| 6,855,129 B2 | * | 2/2005 | Jensen et al. | 604/110 |
| 6,984,223 B2 | * | 1/2006 | Newby et al. | 604/263 |
| 6,986,760 B2 | * | 1/2006 | Giambattista et al. | 604/198 |
| 6,997,913 B2 | * | 2/2006 | Wilkinson | 604/263 |
| 7,004,929 B2 | * | 2/2006 | McWethy et al. | 604/198 |
| 7,198,617 B2 | * | 4/2007 | Millerd | 604/192 |
| 2002/0004648 A1 | * | 1/2002 | Larsen et al. | 604/195 |
| 2002/0010434 A1 | * | 1/2002 | Larsen et al. | 604/241 |
| 2002/0133122 A1 | * | 9/2002 | Giambattista et al. | 604/198 |
| 2003/0014018 A1 | * | 1/2003 | Giambattista et al. | 604/198 |
| 2004/0225262 A1 | * | 11/2004 | Fathallah et al. | 604/198 |
| 2005/0038392 A1 |   | 2/2005 | DeSalvo | 604/198 |

(Continued)

FOREIGN PATENT DOCUMENTS

EP   0 409 180   1/1991

(Continued)

*Primary Examiner*—Kevin C Sirmons
*Assistant Examiner*—Michael J Anderson
(74) *Attorney, Agent, or Firm*—Fitzpatrick, Cella, Harper & Scinto

(57) ABSTRACT

A retracting safety injector pen needle has the needle mounted on a carrier which is movable with respect to the hub, so that the non-patient end of an injection pen needle device is retracted into the hub after an injection for safety.

8 Claims, 2 Drawing Sheets

U.S. PATENT DOCUMENTS

2005/0171485 A1 8/2005 Larsen et al. ............... 604/198
2005/0277895 A1* 12/2005 Giambattista et al. ....... 604/198

FOREIGN PATENT DOCUMENTS

| EP | 0724890 | 8/1996 |
| WO | WO 89/11304 | 11/1989 |
| WO | WO 2004/030539 | 4/2004 |

* cited by examiner

RETRACTING SAFETY PEN NEEDLE

BACKGROUND OF THE INVENTION

1. Field of the Invention

The invention is directed to a passive safety system that may be associated with an injection pen needle to protect a patient and/or healthcare professional using the pen needle from accidental needle sticks. The pen needle according to the invention provides for the non-injection end of a needle in a pen needle to be retracted into the device for safety.

2. Description of the Related Art

Accidental needlestick injuries from contaminated needles expose healthcare workers to the risk of infection from blood-borne pathogens, including the viruses that cause hepatitis B and C, and HIV. According to the Centers for Disease Control and Prevention, healthcare workers in the United States experience an estimated 600,000 exposures to blood each year, with RNs sustaining an overwhelming majority of these incidents.

While the injection device of choice in the U.S. remains the syringe, the demand for pen needles is growing rapidly. The use of self-injection pen needle devices is increasing due to the relative convenience, portability, and ease of use of these devices as compared to single use syringes. Pen needles are also becoming more commonplace in the hospital/clinical setting because certain drugs, such as human growth hormone and osteoporosis medications, are available only in pen needle form.

Healthcare workers have sustained needlestick injuries while removing pen needles from injection devices and subsequently disposing of them after administering an injection to patients. The needles are typically removed after each injection to minimize contamination of the medication in the cartridge and to prevent needle re-use. Removal of the needle generally requires the re-shielding of the injection end (also referred to herein as the "patient end") of the needle using the outer protective cover in which it was supplied. Injuries from the patient end of the needle commonly occur at this time, but they can also occur during the removal of the pen needle from the pen as a result of the exposed non-patient end of the needle. To wholly address the problem of needle stick injuries, it would be desirable to have pen needles with safety features on both ends of the needle.

U.S. Pat. No. 6,986,760 B2, assigned to the assignee of the present application, teaches a pen needle and safety shield system wherein a safety shield, which normally encloses the needle cannula prior to use, permits retraction of the safety shield during injection and automatically extends and locks the shield in the extended enclosed position following use. The pen needle also prevents retraction of the shield during assembly of the shield and needle cannula and hub assembly on the pen injector.

U.S. Pat. No. 6,855,129 B2 discloses a safety needle assembly having a cylindrical housing with a needle mounted thereon for mounting onto a medical injection device. A shield is telescopically movable relative to the housing between a distal position, in which the shield covers the end of the needle, and a proximal position, in which the needle is exposed. A spring located inside the housing urges the shield in the distal direction. A locking element on the device is provided inside the housing with outwardly pointing locking protrusions. The locking element is a separate part provided between the spring and the shield and it is longitudinally moved simultaneously with the shield relative to the housing during use, so that the protrusions on the locking element are guided from a first position where the shield is in the distal position, to a second position where the shield is in the proximal position, to a third position where the locking protrusions are blocked by a blocking surface provided on the inside surface of the housing, so that further movement of the shield is irreversibly immobilized.

In contrast to the prior art, where the needle is fixedly mounted in a hub, in the present invention, the needle is movable with respect to the hub and may thus be retracted to a safe position within the hub after an injection is administered. Thus, the present invention addresses the need for a safety mechanism on the non-patient end of the needle.

SUMMARY OF THE INVENTION

In one aspect of the invention, a non-injection end passive safety system for a pen needle comprises: a) a needle having an injection end and a non-injection end; b) a hub housing the principle components of the device, including a needle carrier and a shield; c) a needle carrier firmly securing the needle, situated in and moving coaxially with respect to the hub; d) a shield having a travel element engaging a corresponding element in the carrier, permitting axial movement of the shield with respect to the carrier and engaging a locking element on the carrier to lock the shield in a position covering the needle; e) a shield return spring biasing the shield in a direction away from the carrier toward the injection end of the needle; and f) a carrier activation spring biasing the carrier in a direction away from the hub in a direction toward to the injection end of the needle. The device is assembled so that, after an injection is administered, the carrier moves the needle toward the injection end and into the body of the hub, effectively storing the needle within the hub to safely shield the needle.

DETAILED DESCRIPTION OF THE PREFERRED EMBODIMENTS

The safety shield system according to the invention is "passive" because the shielding of the non-injection end of the needle is automatic upon administering an injection, as the needle is drawn into the hub. In other words, user-executed steps are not required specifically to shield the needle.

As used herein, the terms "injection end" and "non-injection end" refer to directions on the device, regardless of whether the particular element is involved in the injection. Thus (for example only) the hub and the shield both have an injection end and a non-injection end. The injection end is toward the end of the device that is normally pressed against a patient's body to administer an injection, and the non-injection end is toward the opposite end of the device.

A pen needle is generally longer than it is wide. Movement on the longitudinal axis is referred to herein as "axial" movement. The perpendicular direction is the "radial" direction, and the direction traveled when an element is twisted around the longitudinal axis is the "circumferential" direction. As used herein, the injection or non-injection end of the needle is "covered" when the tip of the end of the needle does not extend beyond the end wall of the shield, or beyond the recess in the hub, notwithstanding that the tip of the needle may be quite close to the aperture in the shield or hub, and exposed to view.

Figure 1:
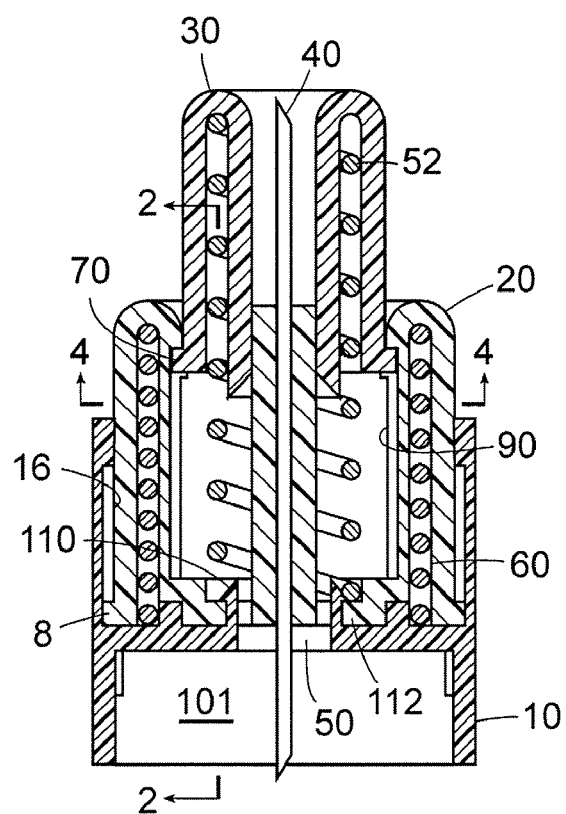
FIG. 1 is a cross section of the injector pen needle showing the hub, carrier and shield.
Figure 3:
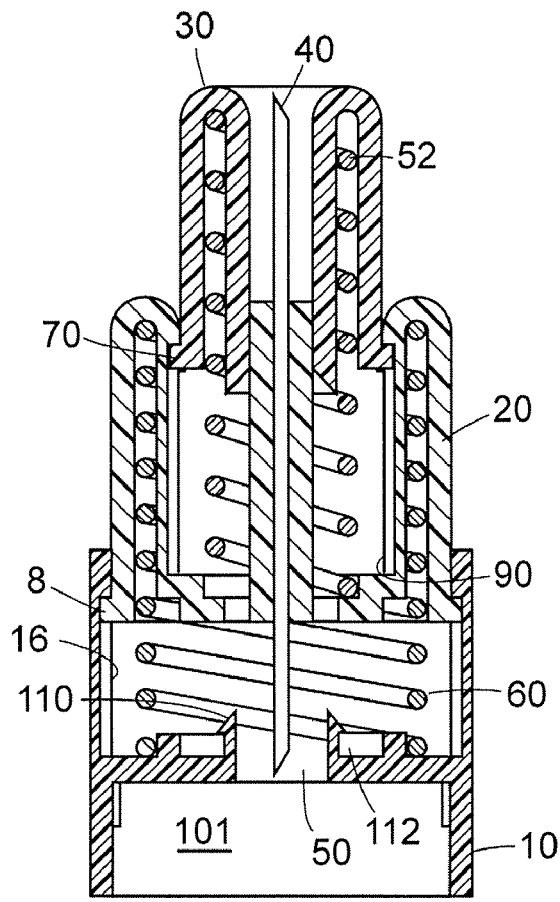
FIG. 3 shows the system of FIG. 1, with the patient-end shield in the full locked out position, and the non-patient end of the needle retracted into the hub.

FIG. 1 illustrates an embodiment of the retracting passive safety shield system according to the invention in the state that it is removed from its packaging and is ready for use. The system includes a hub 10, which attaches to the pen injector (not shown) via recess 101, and houses the other components, including carrier 20, shield 30, and a needle 40. The hub 10 has a recess 101 to receive a pen-injector in the non-injection end, and an aperture 50 to permit passage of the needle 40 into the medication within the pen injector. The term "pen injector" (also sometimes referred to as the "cartridge") may refer to the cartridge housing, or to the housing together with the enclosed medication vial, as the context requires. The needle 40 is securely mounted on the carrier 20, which is situated on the hub 10. The carrier/needle assembly is movable with respect to the hub, as described below.

The materials of construction are not critical. The structural elements, such as the hub, shield and needle carrier are typically injection molded parts, whereas the needle and springs are typically metal.

In FIG. 1, the shield 30 is in an extended position, covering the end of the needle. In use, the shield 30 is forced into the hub to allow injection, compressing spring 52 as the device is pressed against a patient's skin, exposing the needle to the patient's tissue. The spring thereafter exerts force on the shield so that it again covers the injection-end of the needle 40 after injection. The carrier 20 holds the needle 40 firmly in place and is secured to the hub 10 until after injection, when the carrier is released from the hub 10 (as described below), and moves, with the needle 40, toward the injection end and into the body of the hub 10, effectively storing the needle 40 in the hub 10 prior to the user removing the pen injector. This prevents accidental needle sticks that can occur at the non-injection end of the device.

Figure 2:
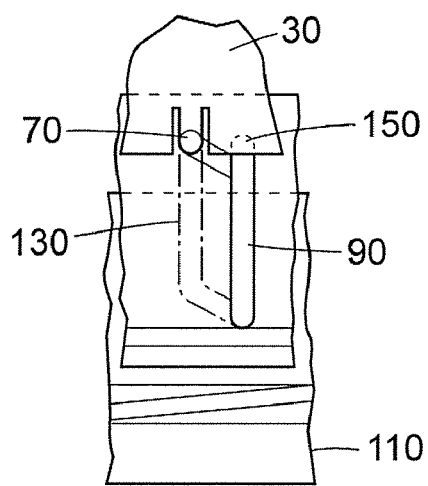
FIG. 2 is a cross sectional detail of the device shown in FIG. 1, viewed along line 2-2, showing the engagement mechanism between the shield and the carrier.

In the initial stages of an injection, shield 30 moves with respect to carrier 20 in an axial direction with a travel element on the shield engaging a corresponding element on the carrier permitting axial movement of the shield with respect to the carrier. For example, the shield may comprise buttons 70 on the base of the shield engaging corresponding tracks 130 and 90 in the carrier, as shown in the details of FIG. 2. As shield 30 is pressed during an injection, the buttons 70 travel in corresponding tracks 130, and at the full travel position, one or more buttons are guided into return track 90. When the shield is fully extended, the shield lock out detent 150 captures the button 70 and locks the shield in place. The buttons 70 are preferably spaced equidistantly around the base of the shield 30, for example, three buttons may be located 120 degrees apart from one another.

Figure 4:
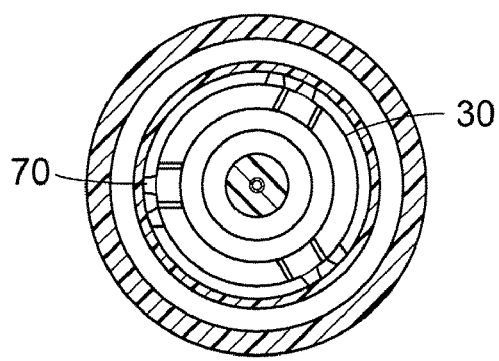
FIG. 4 is a cross sectional detail of the device shown in FIG. 1, viewed along line 4-4, showing the engagement mechanism between the shield and the carrier.
Figure 5:
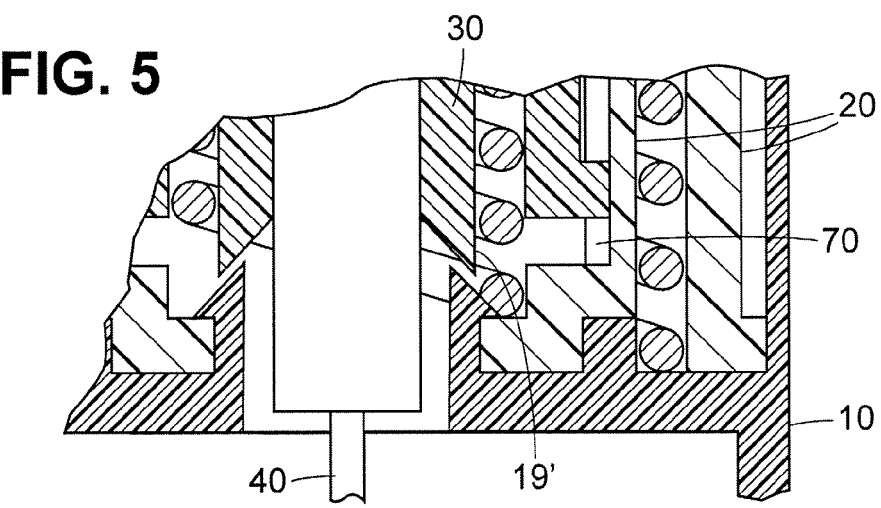
FIG. 5 is a detail showing the mechanism for releasing the carrier from the hub.
Figure 6:
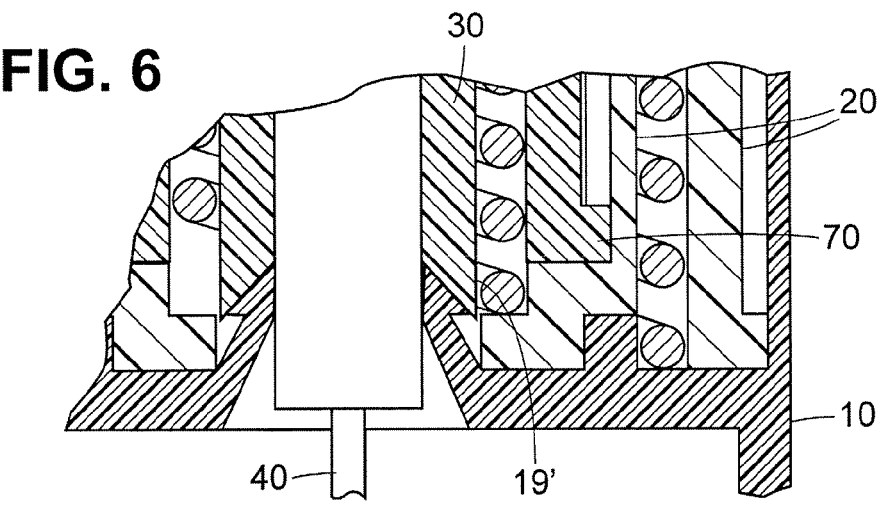
FIG. 6 is a detail showing the mechanism for releasing the carrier from the hub in a released position.

In the embodiments shown, an element on the hub engages with a corresponding element on the carrier to releasably lock the carrier to the hub. "Releasably" in this context means that through the normal operation of the device, the needle carrier is enabled to move axially within the hub. For example, three axially extending tabs 110 on the hub, inboard of the radial side wall of the hub, may engage corresponding edges of through holes 112 on the carrier, fixing the carrier in place while the shield moves axially toward the hub during the initial stages of an injection. Thereafter, as shown in FIG. 4 and FIG. 5, the leading edge 19' of the shield may be shaped to press the tabs 110 inward, freeing the carrier when the shield reaches its full travel position. The force of the spring 60 then forces the carrier toward the injection end, retracting the needle within the hub.

Additionally or as an alternative, through holes or recesses on a radial side wall of the hub may engage corresponding elements on the carrier to releasably lock the carrier to the hub, in such a way that installing the cartridge on the hub (typically, but not necessarily, by rotating the cartridge into a threaded connection, which also rotates the needle carrier) frees the carrier. Thus, the carrier is unlocked in its initial state, held in place by the penetration of the needle into the septum of the cartridge/vial. This feature may be used in the absence of the above-described axially extending lock down tabs 110, or together with the tabs as an additional lock down mechanism.

Figure 7:
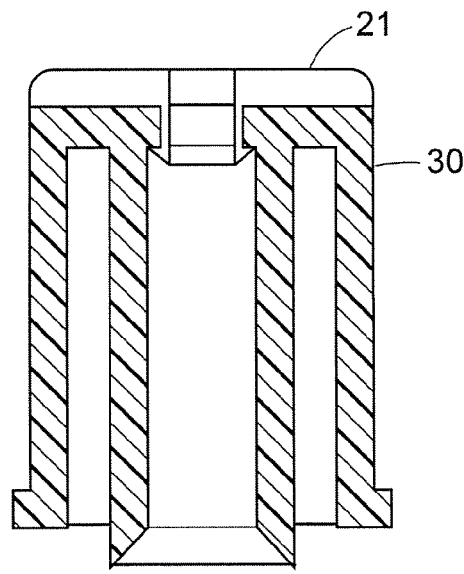
FIG. 7 shows a shield with a shield insert.

During an injection, when the buttons 70 on the shield move in the circumferential direction from axial tracks 130 to track 90 in the carrier 20, the shield will want to rotate a small amount. The distance of circumferential movement may be very small, such as less than 1 mm, and preferably in a range of 0.100 mm to 0.250 mm, but nevertheless perceptible by the user. Any discomfort can be avoided by use of a shield insert 210. As shown in Fig. 7, the shield insert 210 attaches to the shield and is movable with respect to the shield, so that pressed against the skin of a patient during an injection, the shield insert remains stationary while the shield rotates.

This invention can be applied to any injection device incorporating a dual end (injection/non-injection) injection needle configuration, delivering medication (or other substances) into a body space (or other locations) where it would be advantageous to have dual end passive safety features to protect users (self-injectors or health care workers) from accidental needle sticks and exposure to biohazardous substances or other hazardous liquid substances. The examples taken from the preferred embodiments and described above, are for illustration, and are not to be deemed to limit the invention, which is defined by the following claims.

What is claimed is:

1. A non-injection end passive safety system for an injection pen needle, comprising:
   a) a needle having an injection end and a non-injection end;
   b) a hub;
   c) a needle carrier situated in and moving coaxially with respect to the hub and firmly securing the needle;
   d) a shield having a travel element engaging a corresponding element on the carrier permitting axial movement of the shield with respect to the carrier, said travel element engaging a locking element on the carrier to lock the shield in a position covering the injection end of the needle;
   e) a shield return spring biasing the shield in a direction away from the carrier toward the injection end of the needle;
   f) a carrier activation spring biasing the carrier in a direction away from the hub in a direction toward the injection end of the needle;
      wherein the carrier moves the needle toward the injection end and into the hub, effectively storing the needle within the hub to safely shield the non-injection end of the needle after an injection.

2. The system according to claim 1, wherein the travel element on the shield comprises a plurality of buttons positioned around the base of the shield, said buttons engaging tracks running axially on the carrier.

3. The system according to claim 2, wherein said plurality of buttons consists of three buttons.

4. The system according to claim 2, wherein the carrier further comprises at least one detent engaging at least one of said buttons on the shield to lock the shield in a position covering the needle.

5. The system according to claim 1, further comprising a shield insert, the shield insert attaching to the shield and being movable with respect to the shield, so that when pressed against the skin of a patient during an injection, the shield insert remains stationary while the shield is permitted to rotate.

6. The system according to claim 1, further comprising a lock down element on the hub engaging a corresponding element on the carrier, releasably attaching the carrier to the hub.

7. The system according to claim 6, wherein said lock down element is a plurality of axially extending tabs on the hub, inboard of the radial sides of the hub engaging with through holes on the carrier, said tabs flexing upon interaction with the shield to release the carrier.

8. The system according to claim 1, further comprising through holes or recesses on a radial side wall of the hub releasably engaging elements on the needle carrier, adapted so that when a cartridge is installed in the hub, the carrier is released from engagement with the hub.

* * * * *